United States Patent
Hoult et al.

(10) Patent No.: US 9,213,008 B2
(45) Date of Patent: Dec. 15, 2015

(54) DIFFERENTIAL SCANNING CALORIMETRY AND CALIBRATION METHODS FOR USE THEREWITH

(75) Inventors: Robert Alan Hoult, Beaconsfield (GB); Richard Bruce Cassel, Brookfield, CT (US)

(73) Assignee: PERKINELMER SINGAPORE PTE LIMITED, Singapore (SG)

( * ) Notice: Subject to any disclaimer, the term of this patent is extended or adjusted under 35 U.S.C. 154(b) by 859 days.

(21) Appl. No.: 13/145,266

(22) PCT Filed: Jan. 20, 2010

(86) PCT No.: PCT/GB2010/000087
§ 371 (c)(1), (2), (4) Date: Sep. 12, 2011

(87) PCT Pub. No.: WO2010/084313
PCT Pub. Date: Jul. 29, 2010

(65) Prior Publication Data
US 2011/0313713 A1    Dec. 22, 2011

Related U.S. Application Data

(60) Provisional application No. 61/145,773, filed on Jan. 20, 2009, provisional application No. 61/148,876, filed on Jan. 30, 2009.

(51) Int. Cl.
G01N 25/48    (2006.01)

(52) U.S. Cl.
CPC .......... *G01N 25/4866* (2013.01); *G01N 25/486* (2013.01); *G01N 25/4833* (2013.01)

(58) Field of Classification Search
CPC .......... G01N 25/4866; G01N 25/4833; G01N 25/20; G01N 25/486; G01N 25/4893
USPC .............................................. 702/136
See application file for complete search history.

(56) References Cited

U.S. PATENT DOCUMENTS

| | | | | |
|---|---|---|---|---|
| 5,224,775 | A | * | 7/1993 | Reading et al. ................. 374/11 |
| 7,075,652 | B1 | * | 7/2006 | Sarvazyan et al. ............ 356/432 |
| 2004/0001524 | A1 | * | 1/2004 | Jorimann et al. ............... 374/10 |

FOREIGN PATENT DOCUMENTS

WO    2008033361 A2    3/2008

OTHER PUBLICATIONS

Gabbott, Paul, "A Practical Introduction to Differential Scanning Calorimetry," Aug. 2, 2007, pp. 17-18.*

(Continued)

*Primary Examiner* — Sujoy Kundu
*Assistant Examiner* — Liam R Casey
(74) *Attorney, Agent, or Firm* — Cantor Colburn LLP

(57) ABSTRACT

Certain embodiments herein are directed to a differential scanning calorimeter comprising a sample holder thermally coupled to a first furnace, a reference holder thermally coupled to a second furnace, and a processor electrically coupled to the first furnace and the second furnace, the processor configured to receive data during a scan of a sample to provide a heat flow trace and further configured to subtract a calculated baseline from the heat flow trace, the calculated baseline comprising the sum of an isothermal baseline function, a scanning baseline function and a transient baseline function. Calibration methods are also described.

18 Claims, 7 Drawing Sheets

(56) References Cited

OTHER PUBLICATIONS

Dong et al. "Nonlinear Principal Component Analysis—Based on Principal Curves and Neural Networks," Computers chem. Engng vol. 20, No. 1, 1996, pp. 65-78.*

Savitsky et al. "Smoothing and Differentiation of Data by Simplified Least Squares Procedures," Anal. Chem. 1964, 36, pp. 627-1639.*

Gutierrez-Osuna et al. "Transient response analysis for temperature-modulated chemoresistors," Sensors and Actuators B 93 (2003), pp. 57-66.*

Madsen et al. "Singular Value Decomposition and Principal Component Analysis," Feb. 2004, pp. 1-5.*

PCT International Search Report and Written Opinion for International Application No. PCT/GB2010/000087; International Filing Date: Jan. 20, 2010; 9 pgs.

* cited by examiner

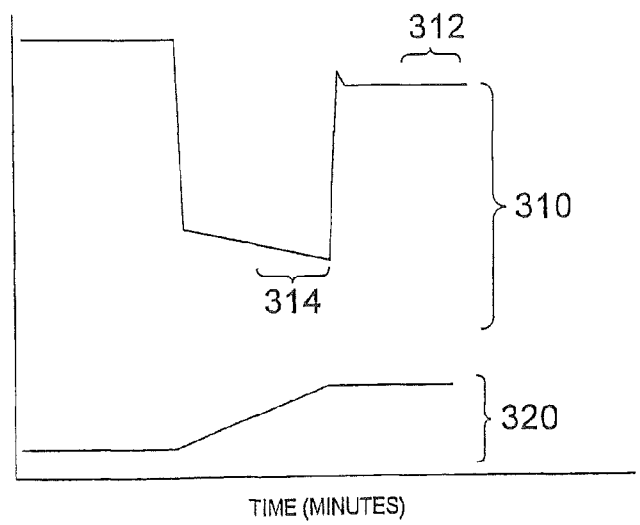
FIG.3
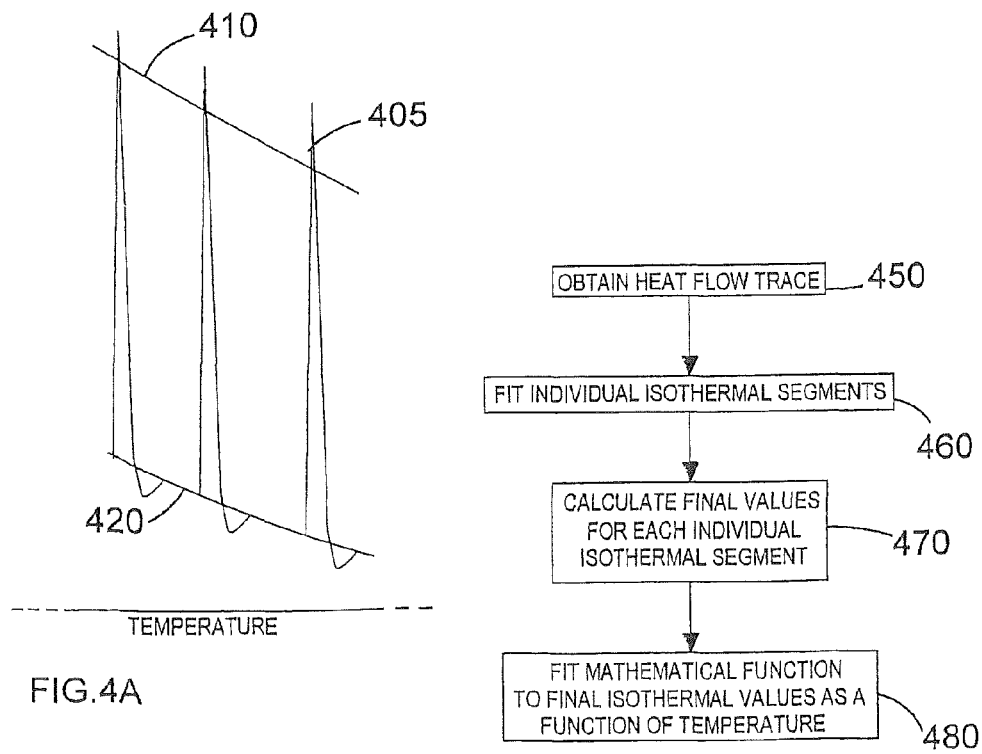
FIG.4A
FIG.4B

DIFFERENTIAL SCANNING CALORIMETRY AND CALIBRATION METHODS FOR USE THEREWITH

CROSS REFERENCE TO RELATED APPLICATIONS

This application claims priority to International Patent Application No. PCT/GB2010/000087, filed Jan. 20, 2010, which claims priority to each of U.S. Provisional Application No. 61/145,773 filed on Jan. 20, 2009 and U.S. Provisional Application No. 61/148,876 filed on Jan. 30, 2009, the entire disclosure of each of which is hereby incorporated herein by reference for all purposes.

TECHNOLOGICAL FIELD

Certain features and aspects disclosed herein relate generally to calorimetry. In particular, certain embodiments are directed to calibrations methods that can be used with a differential scanning calorimeter.

BACKGROUND

Calorimetry is a technique by which the amount of heat required or produced during a chemical reaction or physical process can be measured. Differential scanning calorimetry (DSC) is a thermoanalytic technique in which the difference in the amount of heat required to increase the temperature of a sample and a reference are measured as a function of temperature. The sample and the reference are maintained at substantially the same temperature throughout the experiment. Typical applications of DSC are in the study of phase transitions such as melting, glass transitions, and exothermic reactions. These transitions involve energy changes or heat capacity changes that can be detected by DSC with good sensitivity.

SUMMARY

In one aspect, a differential scanning calorimeter comprising a sample holder thermally coupled to a first furnace, a reference holder thermally coupled to a second furnace, and a processor electrically coupled to the first furnace and the second furnace, the processor configured to receive data during a scan of a sample to provide a heat flow trace and further configured to subtract a calculated baseline from the heat flow trace, the calculated baseline comprising the sum of an isothermal baseline function and a scanning baseline function.

In a preferred embodiment the calculated baseline also includes a transient baseline function.

In certain examples, the processor can be further configured to receive data during a scan in the absence of a sample to provide a background heat flow trace, to express as mathematical functions the isothermal, scanned and transition components of the background heat flow trace, and to store the mathematical functions as the isothermal baseline function, the scanning baseline function and the transient baseline function. In some examples, the processor is further configured to calculate a baseline using the stored mathematical functions. In certain embodiments, the differential scanning calorimeter can further comprise a first temperature sensor in the first furnace and a second temperature sensor in the second furnace, each of the first and second temperature sensors electrically coupled to the processor. In some embodiments, the stored mathematical functions for each of the isothermal and scanned components are fifth order polynomials.

In another aspect, a differential scanning calorimeter comprising a furnace comprising a sample space, a reference space, a first heating element in thermal communication with the sample space and a second heating element in thermal communication with the reference space, and a processor electrically coupled to the first and second heating elements and configured to detect a difference in power provided to the first and second heating elements at each of a plurality of different temperatures within a temperature range to provide a heat flow trace in the absence of any sample and within the temperature range, the processor further configured to provide a mathematical fit for an isothermal and a scanned component of the heat flow trace is described. Preferably the processor is further configured to provide a mathematical fit for a transient component of the heat flow trace.

In certain embodiments, the differential scanning calorimeter further comprises a computer readable medium electrically coupled to the processor and configured to store the provided mathematical fit for each of an isothermal, a scanned and a transition portion of the heat flow trace. In other embodiments, the processor is further configured to generate a baseline using the mathematical fit for each of the isothermal, the scanned and the transition components of the heat flow trace and to subtract the generated baseline from a sample heat flow trace obtained in the presence of a sample. In additional examples, the mathematical fit for each of the isothermal and scanning components is a fifth order polynomial. In some embodiments, the stored transient component is determined using principal components analysis.

In an additional aspect, a method of characterizing the baseline of a differential scanning calorimeter comprising obtaining from the calorimeter a heat flow trace over each of a number of different temperature intervals with no sample present, the temperature being alternately scanned and then held constant at a number of different temperatures for a time sufficient for thermal equilibrium to be achieved, and expressing as mathematical functions the isothermal and scanned components of the trace is disclosed.

In certain embodiments, the method comprises expressing the transient component of the trace as a mathematical function. Preferably all of the calculated functions are stored on a computer readable medium. In some examples, each of the isothermal and scanned components is expressed as a fifth order polynomial in temperature. In other examples, the transient components are expressed by subtracting from the heat flow trace the calculated isothermal and scanning components, and analyzing the remainder using principal components analysis. In certain examples, the range of temperatures over which the measurements are made spans the normal operating temperature range of calorimeter or some subset thereof.

In another aspect, a method of determining a baseline in a differential scanning calorimeter, the method comprising independently fitting a mathematical function to the isothermal components and the scanned components of a heat flow trace comprising a plurality of heat flow values obtained using no sample and alternately scanning and then holding the temperature constant at a number of different temperatures for a time sufficient for thermal equilibrium to be achieved for each of the heat flow values, and generating a baseline for the differential scanning calorimeter using the fitted mathematical functions is provided.

In certain examples, the mathematical function fitted to each of the isothermal and scanned components is a fifth order polynomial. In some examples, transient components can be expressed by subtracting from the heat flow trace the calculated isothermal and scanning components, and analyzing the remainder using principal components analysis. In certain embodiments, the generated baseline is subtracted from a heat flow trace obtained in the presence of a sample. In additional examples, the generated baseline is stored on a computer readable medium.

In an additional aspect, a method of performing calorimetric measurements in a differential scanning calorimeter, the method comprising scanning over a temperature range in the absence of a sample to provide a heat flow trace comprising a plurality of heat flow values obtained by alternately scanning and then holding the temperature constant at a number of different temperatures for a time sufficient for thermal equilibrium to be achieved for each of the heat flow values, fitting an isothermal and a scanned portion of the heat flow trace to a mathematical function, storing the fitted mathematical functions and using the stored fitted mathematical functions to generate a baseline signal for use in the calorimetric measurements is disclosed.

In another aspect, a differential scanning calorimeter comprising furnace means for heating a sample and a reference, and processing means coupled to the furnace means, the processing means having been calibrated by a method described herein is provided.

In yet another aspect of the invention there is provided a method of characterising the baseline of a differential scanning calorimeter comprising: obtaining from the calorimeter a heat flow trace over each of a number of different temperature intervals with no sample present, the temperature being held constant a number of different temperatures for a time sufficient for thermal equilibrium to be achieved, expressing as mathematical functions the isothermal, scanned and transition portions of the trace, and storing said functions.

Additional aspects, examples, embodiments and features are described herein.

BRIEF DESCRIPTION OF THE FIGURES

Certain illustrative features, aspect, embodiments and examples are described in detail below with reference to the accompanying drawings in which:

FIG. 3 shows a portion of an overall heat flow trace and a portion an overall temperature ramp, in accordance with certain examples;

FIG. 4A shows heat flow values at each isothermal temperature plotted as a function of temperature and also shows the fitted heat capacity times the scan rate plus the isothermal baseline, in accordance with certain examples;

FIG. 4B is a flow chart of a method that can be used to obtain the fitted isothermal baseline component, in accordance with certain examples;

Figure 1:
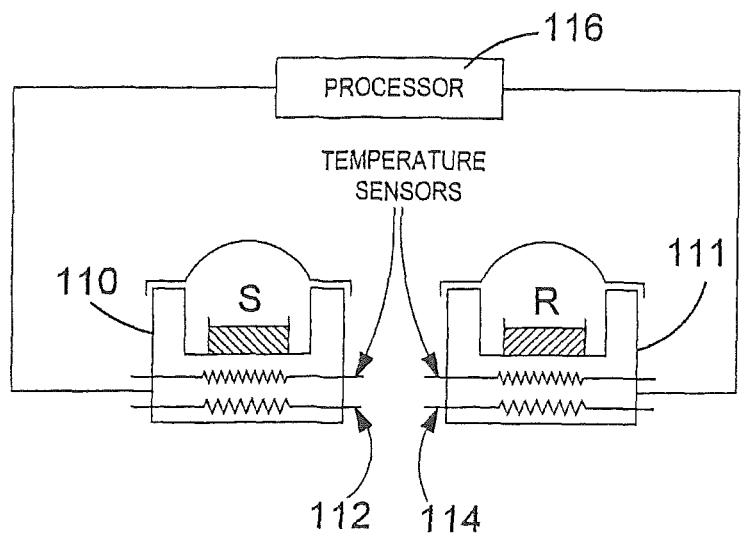
FIG. 1 is a schematic illustration of a portion of a differential scanning calorimeter, in accordance with certain examples.

It will be recognized by the person of ordinary skill in the art, given the benefit of this disclosure that not all of the components of the calorimeter are shown in the figures. In addition, hardware, software or both can be used to implement the calibration methods described below.

DETAILED DESCRIPTION

The calorimetric systems described below are illustrative of those calorimetric systems that can be used with the methods and devices described herein.

There are two principal types of DSC systems in common use. In one, known as power compensation DSC, the temperatures of the sample and reference are controlled independently using separate identical furnaces. The temperatures of the sample and reference are made identical by varying the power input to the two furnaces. The energy required to do this is a measure of the enthalpy or heat capacity changes in the sample relative to the reference.

In the second type of system, known as heat flux DSC, the sample and reference are connected by a low resistance heat flow path typically a metal disc. The assembly is enclosed in a single furnace. Enthalpy or heat capacity changes in the sample cause a difference in its temperature relative to the reference. The temperature difference between sample and reference sensor is recorded and related to enthalpy change in the sample using calibration experiments.

In an instrument for performing DSC, the thermal properties of the sample furnace are desirably identical to those of the reference furnace so that any difference in behavior can be attributed to the presence of the sample, thereby allowing direct observation of the thermal properties of the sample without the need for correction. Such ideal matching is not however practical due principally to three broad classes of differences. There are difference in thermal loss, differences in thermal capacity, and differences in response time.

The effect of these differences can be distinguished in the results of a scan. A difference in response time will lead to a significant transient impulse in the output at any change of scan speed particularly when changing from isothermal (constant temperature) to temperature scanning. This transient dies away in a few seconds, but can obscure real features at the start or end of the scan. Differences in thermal loss can cause either unwanted temperature differences and/or a differences in heat flow between the two furnaces. This result typically is dependent on temperature although the dependence may change slowly with time as the emissivity changes over long periods. Differences in thermal capacity may also cause unwanted temperature differences and/or differences in heat flow. However these differences scale with the scan rate and are zero under isothermal conditions.

In practical systems it is conventional to take what is known as a baseline scan—a scan with no sample present. This baseline should ideally be flat, but in practice suffers from several perturbations. There are short lived transients that occur after transition from isothermal to scanning and vice versa, curvature of the baseline which is independent of the scan rate and is only a function of temperature, and further curvature of the baseline which is scan rate dependent.

Attempts have been made to correct these perturbations in hardware, in particular electronically. For example, a deliberate offset in temperature between sample and reference can be used to effect a change in slope of the baseline. However it is difficult with hardware compensation to achieve the degree of flexibility needed to produce a flat baseline under all conditions.

One software correction method which is used is to measure a baseline without a sample and subtract that baseline from subsequent sample scans. This works well if the baseline remains substantially constant from run to run, but has the disadvantage that the baseline must be rerun every time the scan conditions are changed, which can be time consuming.

In certain embodiments described herein, the baseline can be characterized by a function of temperature, scan speed and time, and the resulting measurements can be used to provide an extrapolated baseline, based on the particular conditions used, that can be used when calorimetric measurements are altered.

In certain examples, a method to provide a baseline can include obtaining a heat flow trace over each of a number of temperature intervals with no sample present, the temperature being then held substantially constant at each of a number of different temperatures for a time sufficient for thermal equilibrium to be achieved, expressing as mathematical functions the isothermal, scanned and transition segments of the trace, and storing the functions. A baseline may be represented to a good approximation by a sum of mathematical functions representing the isothermal and scanned segments of the trace. In preferred embodiments the baseline also includes a mathematical function representing transient segments of the trace because otherwise interesting features in the heat flow trace may be obscured by transients.

In certain examples, the isothermal segments may be expressed as a polynomial in temperature. The scanned segments may also be expressed as a polynomial in temperature. The polynomials may be higher order polynomials, for example, those that are third order or higher, e.g., fourth or fifth order polynomials.

In some examples, the transient segments can be expressed by subtracting from the heat flow trace the calculated isothermal and scanned segments, and analyzing the remainder using principal components analysis.

In certain embodiments, the range of temperatures over which the measurements are made may span the normal operating temperature range of the calorimeter or some subset thereof.

Certain embodiments are also directed to a differential scanning calorimeter comprising furnace means for heating a sample and a reference, and processing means, coupled to the furnace means, the processing means having been calibrated by a method defined herein.

Referring now to FIG. 1, a schematic illustration of a differential scanning calorimeter 100 is shown. It comprises a first furnace 110, which contains an encapsulated sample to be analyzed and a second furnace 111, which contains a reference sample, usually an empty capsule. Each of the furnaces 110 and 111 includes its own heater 112 and 114, respectively. The furnaces 110 and 111 are electrically coupled to a processor 116, which can be used to control the furnaces and also to process measured data.

In order to interpret a DSC measurement when a sample is present, it is desirable to first record a baseline of the instrument. In the present arrangement, the instrument can be calibrated to provide stored data that enables the baseline to be computed for each measurement. A conventional calibration process is as follows: In the calibration procedure the instrument baseline is characterized as a function of program temperature, scan speed and time in order to identify the behavior of the three types of imbalance between the sample and reference discussed herein. While it is possible to carry out a large number and variety of scan types in order to encompass the entire behavior, a single step scan is typically performed.

In such a step scan the temperature of the sample furnace with no sample present is initially held constant until thermal equilibrium is achieved. The temperature is then increased at a steady rate to a new temperature and held constant again. This process is repeated incrementally for the whole temperature range of a typical scan. The entire temperature range of the instrument is covered at a moderate step scan speed of around, for example, 10-50° C. per minute, e.g., 20° C. per minute, in scanning and isothermal periods of around 0.5-3 minutes, e.g., about 1 minute. This period is desirably long enough to capture the full duration of the transient caused by the change of scan speed.

Figure 2:
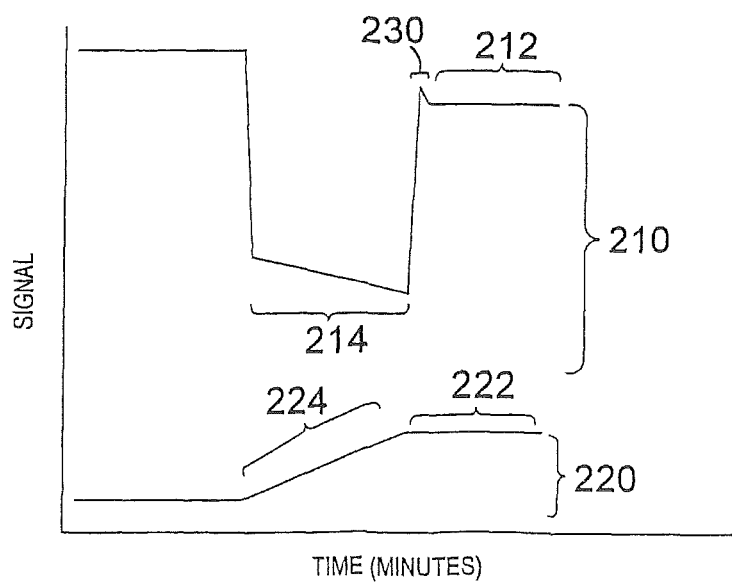
FIG. 2 is a prophetic graph showing a heat flow trace and a temperature program, in accordance with certain examples.

In certain examples and referring to FIG. 2, a portion of a prophetic heat flow trace 210 from a calibration run and a corresponding temperature ramp curve 220 are shown. The particular shapes, isothermal times, temperature ramp times and the like are not limiting and are provided here to facilitate discussion of the devices and methods described herein and to provide a more user friendly description of certain portions of a heat flow trace that are referred to herein. In certain embodiments, the heat flow trace 210 may be divided into three different components. An isothermal component 212 corresponds to an isothermal segment 222 of the temperature ramp curve 220. A scanning or scan segment 214 corresponds to a linear ramp of temperature 224 in the temperature ramp curve 220. A transient component 230 corresponds to the remainder of the heat flow trace if the isothermal components and scan components are subtracted from the heat flow trace 210, e.g., the heat flow trace less the isothermal components and the scan components. The transient component can occur for several reasons as discussed herein. For example, a difference in response time can lead to a significant transient impulse in the output at any change of scan speed particularly during the transition from isothermal to temperature ramping in the temperature ramp curve. This transient component decays quickly, but it can obscure real data at the start or the end of a temperature ramp. The heat flow trace 210 includes enough information for calculation of a baseline at a selected scan rate and over a selected temperature range. The isothermal components delineate the baseline at zero scan speed. The scan components (after the transient component) delineate the baseline at a finite scan speed allowing a difference in thermal capacity to be determined. Each transition from scan to isothermal or isothermal to scan can generate a transient at a specific temperature.

In accordance with certain embodiments, the different components reflected in the heat flow trace can be approximated using a suitable mathematical function. The exact mathematical function may depend on a desired fit. In certain examples, the different isothermal components together can provide an isothermal baseline which can be approximated using a suitable mathematical function. Similarly, the different scan components together can be used together to provide a heat capacity baseline which can be approximated using a suitable mathematical function, which may be same or may be a different mathematical function than the one used to approximate the isothermal components. In certain embodiments, the isothermal and heat capacity baselines each can be independently fit to a fourth order or higher order polynomial, a cubic spline, fifth order polynomial, or any other suitable mathematical expansion. In certain examples, each of the isothermal and scan baselines may be approximated using a fifth order polynomial. The resulting equation for each of the isothermal and scan baselines can be subtracted from a heat flow trace to provide a transient baseline as described in more detail below.

In certain embodiments, the resulting transients can be analyzed by approximating them as a sum of common factor curves using a principal components analysis. Principal components analysis is a common mathematical operation where a number of possibly correlated variables are transformed into a smaller number of uncorrelated variables called principal components. The first principal component is selected to account for the largest amount of the variability in the data, and each succeeding component accounts for the remaining variability. In a principal component analysis, the obtained data can be transformed into a new coordinate system such that the greatest variance by any projection of the data comes to lie on the first coordinate (called the first principal component), the second greatest variance on the second coordinate (the second principal component), and so on. The exact number of components used can depend on the desired accuracy or can be truncated at a selected number of components for ease of use.

In one non-limiting example of principal components analysis, data are first obtained, for example, sets of voltage values at correlated times, each set at a specific temperature. The mean voltage value at each time across the temperatures may be subtracted from each corresponding voltage; thus, the mean of the new data set may be forced to be zero. A covariance matrix can then be produced and used to determine the eigenvectors and the eigenvalues of the covariance matrix. The eigenvector with the highest eigenvalue is considered to be the principal component of the data set. Once eigenvectors are found for the covariance matrix, they can be ordered according to eigenvalue, e.g., highest to lowest. The ordering provides the components in order of significance. In certain examples, components beyond the second principal component may be ignored in the transient calculations described herein, though with modern computational systems, third, fourth and higher principal components may be included, with little or no detrimental time effects. From the selected eigenvectors, a feature vector (vector matrix) can be produced. Once the feature vector is formed, the transpose can be multiplied on the left of the original data set, transposed. The end result is that the data is expressed in terms of the selected vectors. This analysis permits expression of the data in terms of the patterns between them, where the patterns are the lines that most closely describe the relationships between the data. Such an expression provides useful information as to how each transient value relates to the other transient values of the heat flow trace. The exact number of principal component factors used can vary, and, in some examples, one, two, three, four, five, six or seven factors can be used. In certain embodiments, two principal component factors can be used to provide a suitable mathematical function for the transient portion of the overall baseline. Of course, principal components analysis is a well known mathematical technique, and, within this umbrella, many different methods may exist for providing a suitable mathematical function to represent transients.

In certain embodiments, a calibration procedure can be performed where a mathematical function is used to approximate the isothermal portions of the heat flow trace. This process is described with reference to FIG. 3. A portion of the overall heat flow trace is shown in FIG. 3 as trace 310. Similarly, a portion of the overall temperature ramp is shown in FIG. 3 as temperature ramp 320. In determining the isothermal baseline, a selected portion of the heat flow trace corresponding to the isothermal component can be used. In this illustration, a segment 312 of the isothermal component is used. Any portion of the isothermal component after the transient may be used, and, in certain examples, the last 75%-10% can be used, for example, the last 50% can be used. It is desirable to use the second half of the isothermal segment to avoid any effects caused by the transients, and in the second half of the isothermal segment, the transients should have decayed and have no effect. The segment 312 can be fit to a mathematical function to smooth the trace. For example, a second order polynomial, third order polynomial or higher order polynomial can be used. The polynomial can be fit as a function of time. As a result of the fitting, the final value of the isothermal segment 312 can be calculated to provide an estimate of the true isothermal heat flow at that particular temperature. This process can be repeated for each of the isothermal portions of a heat flow trace. The resulting final heat flow values may then be evaluated as a function of temperature to obtain an isothermal baseline. For example and referring to FIG. 4A, the heat flow values at each isothermal temperature are shown plotted as a function of temperature. The isotherms, being at constant temperature, are no longer obvious in the heat flow versus temperature trace. The final isothermal points may be fit to a polynomial, e.g., a fifth order polynomial, as shown in the upper curve 410. The influence of transient overshoot is shown where the heat flow curve 405 rises above the fitted curve 410.

In certain examples, the process for determining the isothermal baseline is shown schematically in FIG. 4B. The process includes a first step 450 where a heat flow trace is obtained in the absence of a sample. In a next step 460, individual isothermal segments (or selected portions thereof) of the heat flow trace are fitted to a mathematical function. Following this fit, the final value of each individual isothermal segment is calculated in a step 470. Using the final isothermal segment values at each temperature, a mathematical function can be used to approximate the relationship between the final values of the isothermal segments as a function of temperature in a step 480. This mathematical function represents the isothermal baseline of the heat flow trace.

In certain embodiments, the heat capacity baseline can also be determined in a similar manner. Referring again to FIG. 3, a selected portion 314 of the scan segment can be smoothed similar to the smoothing performed with the isothermal segments. Also, the exact percentage or amount of the scan segment that is used can vary from about 75%-10%, e.g., about 50%, and any amount may be used where the transient has little or no effect. In certain examples, the second half of the scan segment can be smoothed. The exact smoothing function used can vary, and in certain examples, the smoothing function is a second order polynomial, a third order polynomial or a higher ordered polynomial. The final value of the scanned segment at the following isotherm temperature is projected to estimate the true scanning heat flow at that temperature. The isothermal heat flow estimated using segment 314 is then subtracted from the heat flow value obtained using segment 312 to provide a resulting heat flow value. Similar calculations may be performed for each scan segment to provide a plurality of heat flow values. These heat flow values may then be evaluated as a function of temperature. For example, a function can be fitted to the heat flow values as a function of temperature, similar to what is shown in FIG. 4A. The heat flow values can be divided by the scan rate to obtain a fitted function for the heat capacity difference as a function of temperature. In the alternative, the heat capacity difference can be obtained by integrating the heat flow signal over temperature step interval. A curve 420 is shown in FIG. 4A and is a reconstructed scan (minus the transients), being the fitted heat capacity times the scan rate plus the isothermal baseline.

Figure 5:
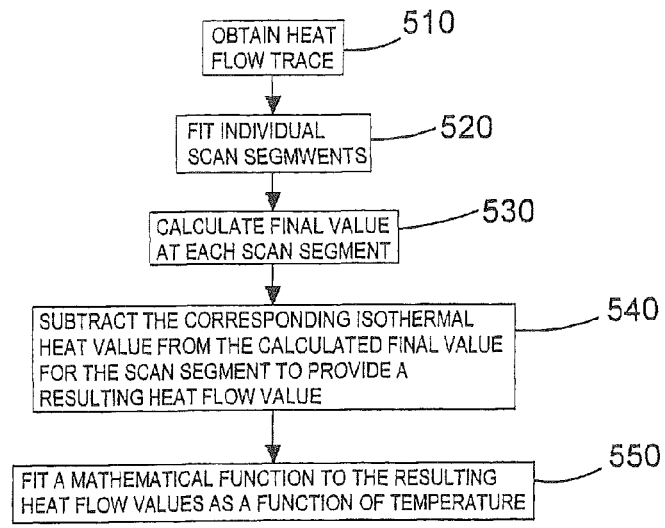
FIG. 5 is a flow chart of a method that can be used to obtain the heat capacity baseline component, in accordance with certain examples.

In certain embodiments, a process for determining the heat capacity baseline is shown schematically in FIG. 5. In a step 510, a heat flow trace is first obtained in the absence of a sample. In certain examples, step 510 and step 460 may be the same step, e.g., two separate heat flow traces are not needed. The individual scan segments of the heat flow trace are separately fitted to a mathematical function in a step 520, and a final value for each scan segment is calculated in a step 530. A resulting heat flow value is then obtained in a step 540 by subtracting a corresponding isothermal heat flow value from a calculated scan segment value, e.g., by subtracting the isothermal heat flow value of segment 214 from the calculated scan segment value of segment 212 in FIG. 2. This step is repeated for each scan-isothermal segment pair in the heat flow trace. Using the resulting heat flow values at each temperature, a mathematical function can be used to approximate the relationship between the resulting heat flow values as a function of temperature in a step 550. This mathematical function represents the heat capacity baseline of the heat flow trace.

In certain examples, the transient component of the baseline can be obtained by subtracting the mathematical function obtained for the isothermal baseline from the heat flow trace. The mathematical function corresponding to the heat capacity contribution obtained from the scan segments is also subtracted from the heat flow trace. The remainder represents the transient components of the heat flow trace.

Figure 6:
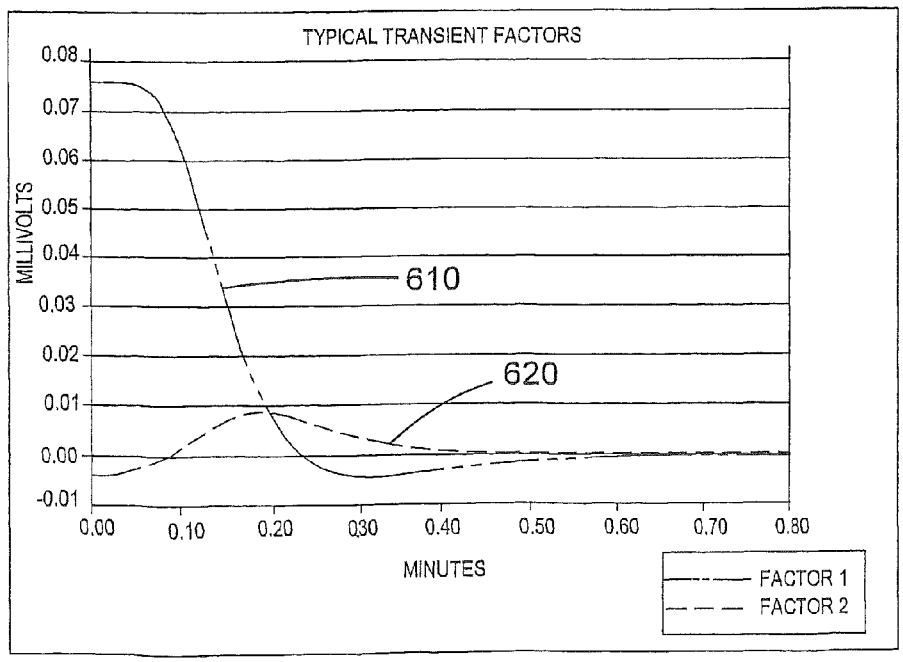
FIG. 6 is a graph showing the first and second principal components of transients, in accordance with certain examples.

In certain embodiments, to calculate the transient components following subtraction of the isothermal and heat capacity baselines from the heat flow trace, the transients may be grouped according to transition direction, e.g., scan to isothermal transients or isothermal to scan transients. The transients can be normalized by dividing by the scan rate. The resulting data is then analyzed by principal components analysis as a function of time retaining typically the first two principal components factors. An illustration of this process is described with reference to FIG. 6. Curve 610 represents one principal component factor and curve 620 a second principal component factor. The factors (coefficients) are expressed as a function of temperature using a fifth order polynomial approximation. It can be seen that the transients persist for an infinite length of time conceptually and therefore it is necessary to truncate them after a reasonable time. An offset equal to the final value of each transient is subtracted from the transient to ensure that no step is observed when the transient is later added to the reconstructed baseline.

Figure 7:
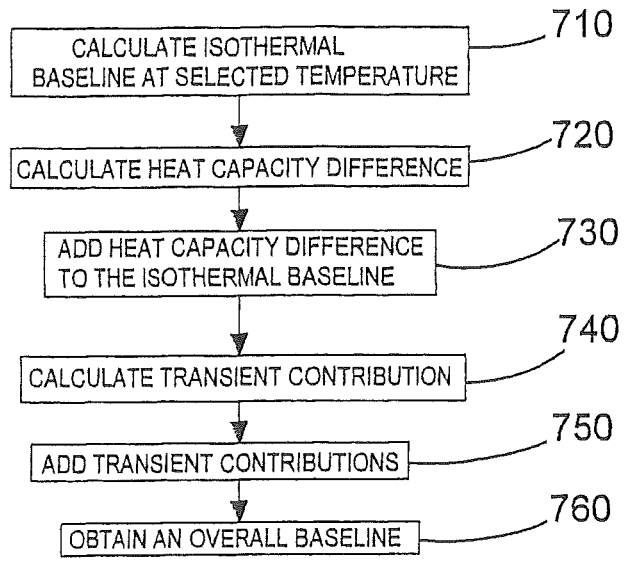
FIG. 7 is a flow chart of a method that can be used to calculate a baseline, in accordance with certain examples.

In certain embodiments, the calibration procedures described above provide the information from which a baseline can be reconstructed for any given scan speed and temperature range. This procedure is shown schematically in FIG. 7. In a first step 710, the isothermal baseline is calculated at a selected program temperature. If scanning is to occur in the instrument, then the heat capacity difference is computed from the heat capacity baseline and multiplied by the scan rate in a step 720. The resulting value is added to the isothermal baseline in a step 730. The transient contribution is then added at a step 740. The particular transient contribution can be computed from the factors evaluated at the appropriate time after the change, interpolating as necessary, and scaled by the coefficients computed from their curves and multiplied by the scan rate in a step 750. Once calculated, the transient contribution can be added to the baseline from step 730 to obtain an overall baseline at a step 760.

This procedure described above for representing the calibration data has been selected primarily for its efficiency. It will be appreciated that there are other compression and interpolation schemes that could be used instead. For example, the fifth order polynomial fitting could be replaced by cubic splines or by fitting other types of function or by any sensible interpolation scheme. The transient behavior should strictly speaking be represented as a convolution of the program temperature with some instrument response function and there are a number of ways in which such a function of time and temperature can be modelled. In the method described above the approach is relatively simple to implement and works satisfactorily.

In accordance with one or more embodiments, the procedure may be modified with minor calculation changes to accommodate multiple scan rates, such as alternating between two scan rates. In some embodiments, a first scan rate may be slower than a second scan rate, such as to accommodate heating or cooling. In accordance with one or more embodiments, non-transient calibration may be implemented. In at least one embodiment, non-transient analysis may be used for calibration in differential scanning calorimetry.

In accordance with certain examples, the devices and systems disclosed herein may be controlled or used with at least in part, a processor which can be integrated into the calorimeter or part of a separate computer system electrically coupled to the calorimeter. The processor or computer systems may be, for example, general-purpose computers such as those based on Unix, Intel PENTIUM-type processor, Motorola PowerPC, Sun UltraSPARC, Hewlett-Packard PA-RISC processors, or any other type of processor. It should be appreciated that one or more of any type computer system may be used according to various embodiments of the technology. Further, the system may be located on a single computer or may be distributed among a plurality of computers attached by a communications network. A general-purpose computer system according to one embodiment may be configured to perform any of the described functions including but not limited to: data acquisition, autosampler control, furnace temperature control, data logging, data analysis, baseline calculations and the like. It should be appreciated that the system may perform other functions, including network communication, and the technology is not limited to having any particular function or set of functions.

For example, various aspects may be implemented as specialized software executing in a general-purpose computer system. The computer system may include a processor connected to one or more memory devices, such as a disk drive, memory, or other device for storing data. The memory is typically used for storing programs and data during operation of the computer system. Components of computer system may be coupled by an interconnection mechanism, which may include one or more busses (e.g., between components that are integrated within a same machine) and/or a network (e.g., between components that reside on separate discrete machines). The interconnection mechanism enables communications (e.g., data, instructions) to be exchanged between system components. The computer system typically is electrically coupled to an interface on the calorimetric device, and/or additional devices in the case of hyphenated systems, such that electrical signals may be provided from the calorimetric device to the computer system for storage and/or processing.

The computer system may also include one or more input devices, for example, a keyboard, mouse, trackball, microphone, touch screen, and one or more output devices, for example, a printing device, status or other LEDs, display screen, speaker. In addition, the computer system may contain one or more interfaces that connect the computer system to a communication network (in addition or as an alternative to the interconnection mechanism). The storage system of the computer typically includes a computer readable and writeable nonvolatile recording medium in which signals are stored that define a program to be executed by the processor or information stored on or in the medium to be processed by the program. For example, the temperature profile, the calculated isothermal baseline, heat capacity baseline and/or transient factors can be stored on the computer readable medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in storage system, as shown, or in memory system. The processor generally manipulates the data within the integrated circuit memory and then copies the data to the medium after processing is completed. A variety of mechanisms are known for managing data movement between the medium and the integrated circuit memory element, and the technology is not limited thereto. The technology is not limited to a particular memory system or storage system.

The computer system may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the computer system described above or as an independent component.

In some examples, the computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used. In addition or alternative to a processor, the computer system may include a controller such as for example and 8-bit or 16-bit controller such as SAB-C517A (commercially available from Infineon) or ST10C269 (commercially available from ST-Microelectronics), respectively. Other controllers such as 32-bit or higher controllers may also be used in place of a processor or in addition to the processor of the computer system.

The processor and operating system together define a computer platform for which application programs in high-level programming languages are written. It should be understood that the technology is not limited to a particular computer system platform, processor, operating system, or network. Also, it should be apparent to those skilled in the art that the present technology is not limited to a specific programming language or computer system. Further, it should be appreciated that other appropriate programming languages and other appropriate computer systems could also be used.

In certain examples, the hardware or software is configured to implement cognitive architecture, neural networks or other suitable implementations. For example, a database of known temperature profiles may be linked to the system to provide access to known thermal properties for a class of substances. Such configuration would allow for storage and access of a large number of materials whose thermal properties are known, which can increase the functionality of the devices and systems disclosed herein.

One or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

Various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various aspects may be implemented in a non-programmed environment (e.g., documents created in HTML, XML or other format that, when viewed in a window of a browser program, render aspects of a graphical-user interface (GUI) or perform other functions). Various aspects may be implemented as programmed or non-programmed elements, or any combination thereof.

In certain examples, a user interface may be provided such that a user may enter desired start and stop temperatures, scanning rates, autosampling rates and the like. Other features for inclusion in a user interface will be readily selected by the person of ordinary skill in the art, given the benefit of this disclosure. In some examples, the user interface may be one such as the one commonly found on Pyris, Spectrum Express, or Chromera software commercially available from PerkinElmer, Inc. Other suitable software interfaces may also be used depending on the intended use of the calorimetric device and any devices to which it is coupled. The baseline procedures described herein can be downloaded or added to existing software packages to facilitate baseline determinations without having to purchase new instruments or new software packages.

In certain embodiments, a calorimetric system can retrieve the isothermal, heat capacity and transient baseline components from a remote server for a particular instrument. For example, these values may be determined prior to shipping of the device and can be remotely sent to the device prior to use to facilitate ease of use by the end-user. The instrument may be bar coded or otherwise include a unique identifier such that the proper baseline parameters are provided by the remote server.

In some examples, the baseline procedures described herein can be used in combination with conventional scanning methods where a background scan is run prior to sampling. For example, the calculated baseline can be subtracted from sample heat flow trace and compared to a corrected sample heat flow trace where the actual background scan has been performed by an end-user. Such comparison can provide for additional quality control and can provide for the appearance of data that might be obscured in the transient portion of the scan.

Figure 8:
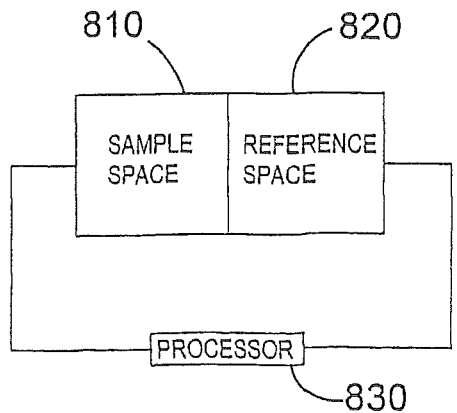
FIG. 8 is a block diagram of a calorimeter, in accordance with certain examples.

In some embodiments, a calorimeter that includes a processor configured or programmed to implement the methods described herein is provided. Referring to FIG. 8, the calorimeter 800 includes a sample space or holder 810, and a reference space or holder 820. Each of the sample space 810 and the reference space 820 includes a respective heating element which may be a furnace or other heating devices commonly used in calorimetric devices. The sample space 810 and the reference space 820 are each electrically coupled to a processor 830. For example, temperature sensors (not shown), the furnace or other components may be electrically coupled to the processor 830 such that a temperature scan can be implemented and resulting heat flow values can be obtained.

Example 1

Figure 9:
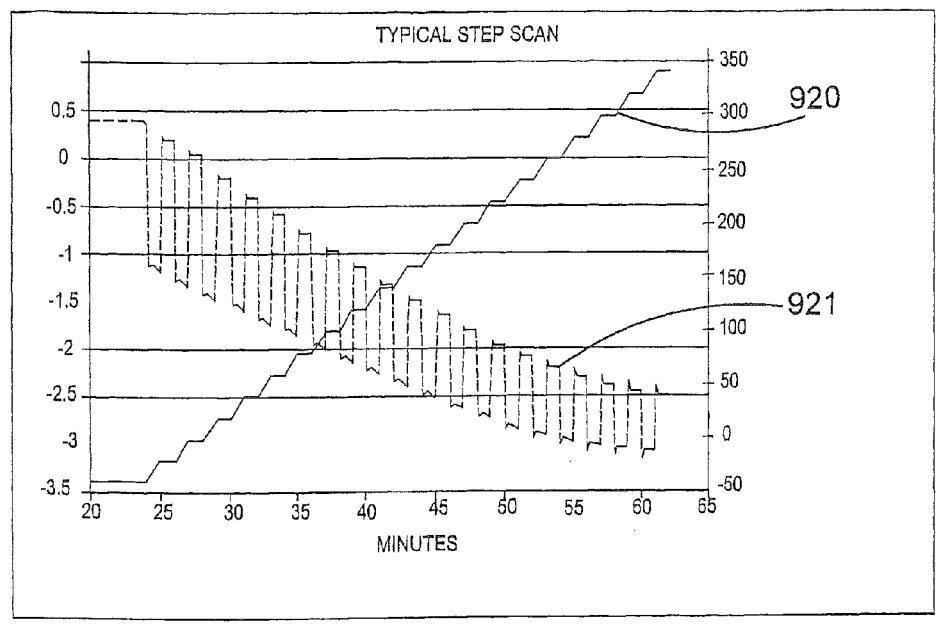
FIG. 9 shows a typical step scan used in a calibration process, in accordance with certain examples.

In one illustration, the temperature of a sample furnace with no sample present is initially held constant until thermal equilibrium is achieved. The temperature is then increased at a steady rate to a new temperature, and the new temperature is maintained for a selected period. This process is repeated incrementally for a whole temperature range of a typical scan. For example, a step scan speed of around 20° C. per minute with isothermal periods of about 1 minute can be used. The isothermal period can be sufficiently long to capture the full duration of the transient caused by the change of scan speed. The resulting step scan is illustrated in FIG. 9. A curve 920 represents the temperature, while a curve 921 is a heat flow trace. The heat flow trace 921 includes all the information to reconstruct a baseline to good accuracy under most scan conditions.

Figure 10:
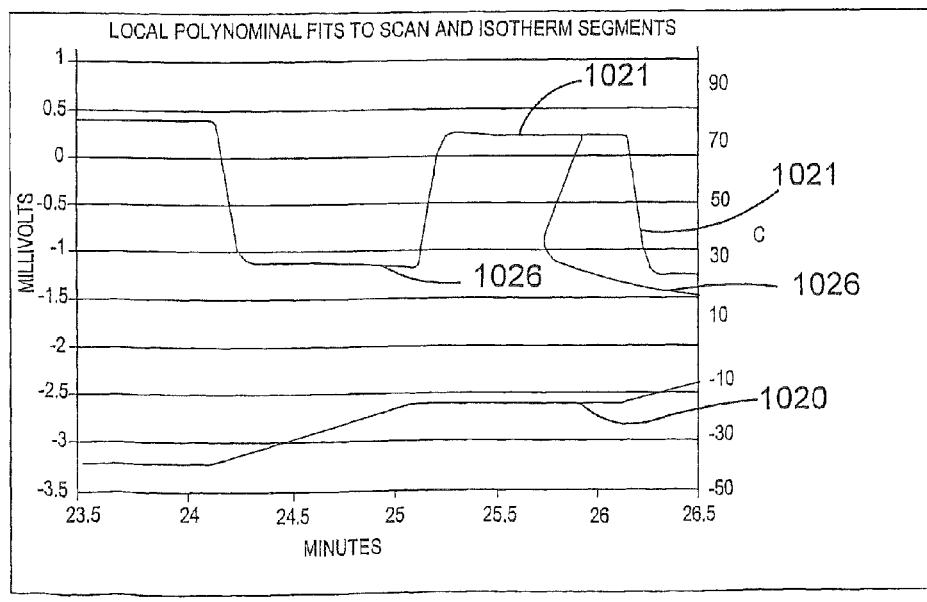
FIG. 10 shows a polynomial fits to scan an isotherm segments, in accordance with certain examples.

For the isothermal baseline component, the second half of the isothermal segments shown in FIG. 9 can be fitted to a second order polynomial in time to those segments of the heat flow trace 921. This result is shown in FIG. 10, where the heat flow trace 1021 and the polynomial fit 1026 are shown. The temperature ramp is shown as curve 1020.

Figure 11:
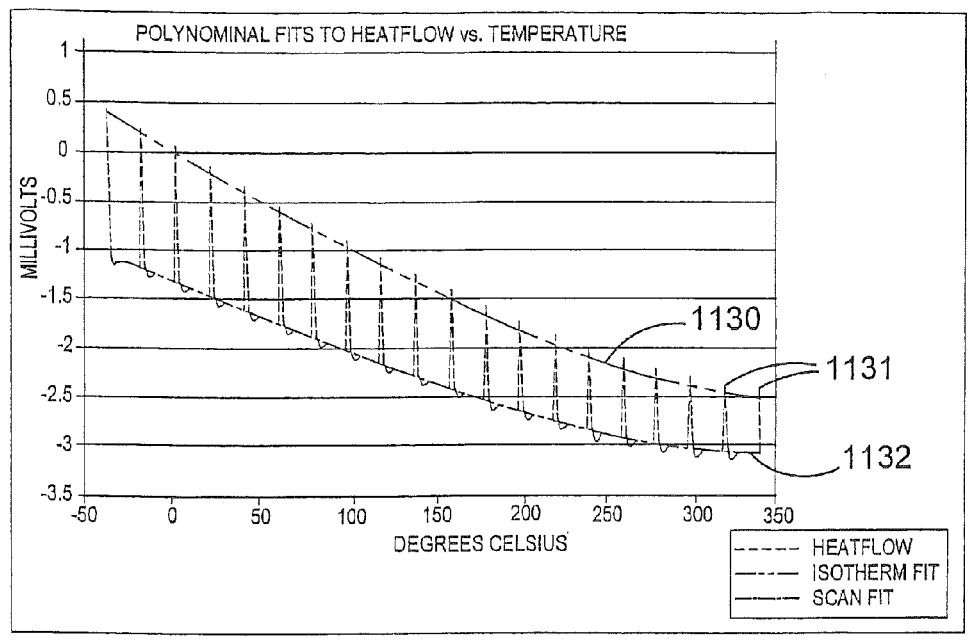
FIG. 11 shows the fitting of polynomials to the heat flow as a function of temperature, in accordance with certain examples.

The next step is to compute the final value of the isothermal segments to estimate the true isothermal heat flow at that temperature. The obtained heat flow values are fitted for each isothermal with a fifth order polynomial in temperature. The result is shown in FIG. 11. The curve 1130 is a fifth order fit to the isothermal points. The influence of transient overshoot can be seen where the heat flow curve 1131 rises above the fitted line. The lower curve 1132 is the reconstructed scan minus transients and is the fitted heat capacity multiplied by the scan rate plus the isothermal baseline.

To determine the heat capacity baseline component, the second half of the scanned segment of the heat flow curve subsequent to a transient can be smoothed by fitting a second order polynomial in temperature as shown in FIG. 10. The final value of the scanned segment of the immediately following isotherm temperature is projected to estimate the true scanning heat flow at that temperature. The local estimate of the heat flow is subtracted and the obtained heat flows values for each scanned segment are fitted with a fifth order polynomial in temperature as shown in FIG. 11. The obtained values can be divided by the scan rate in order to obtain a polynomial for the heat capacity difference as a function of temperature.

Figure 12:
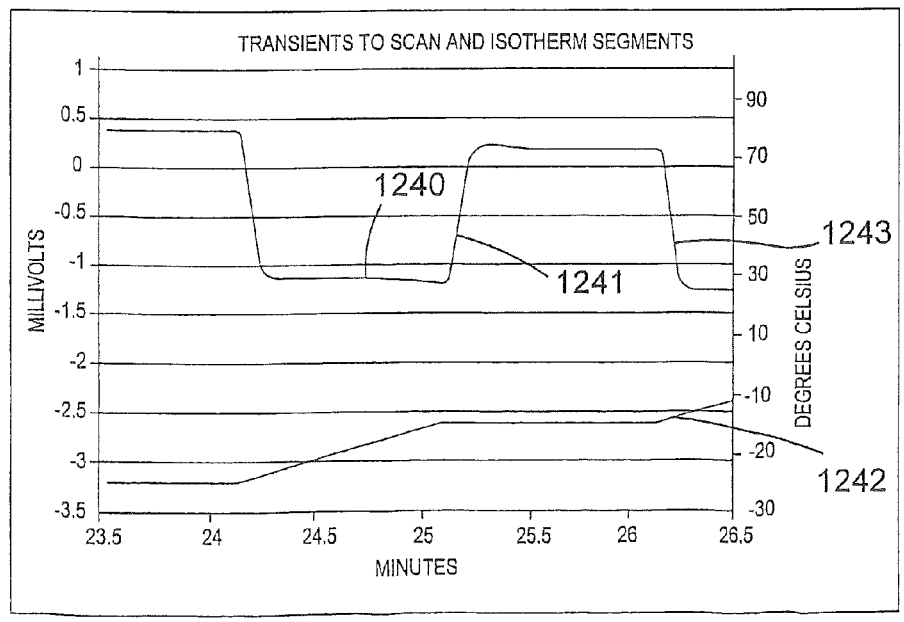
FIG. 12 shows transients of scan and isotherm segments, in accordance with certain examples.
Figure 13:
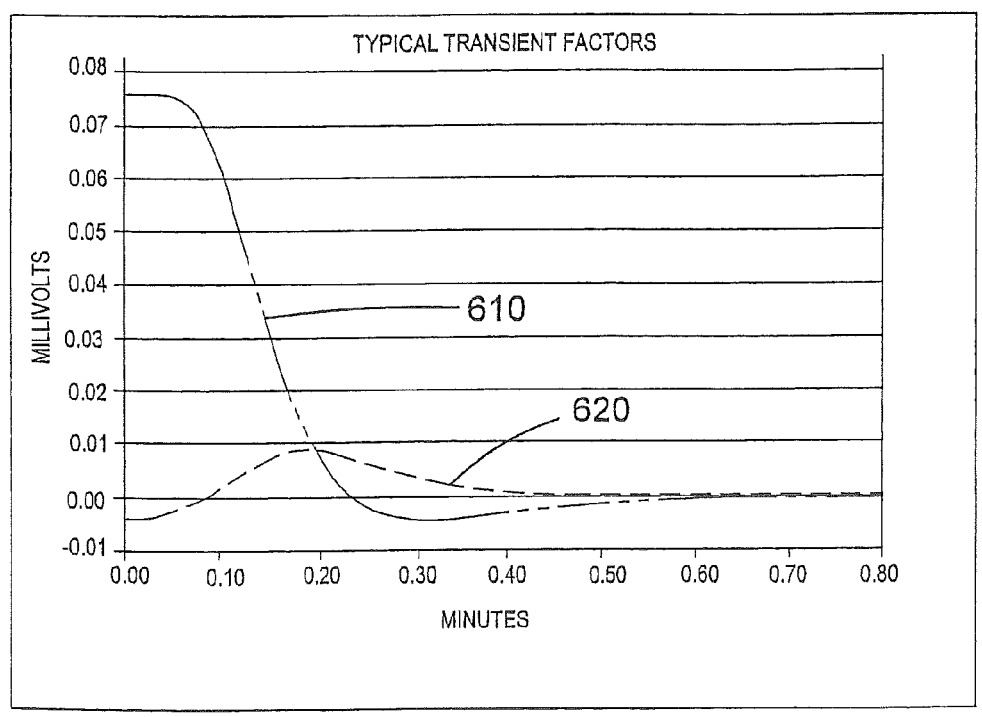
FIG. 13 shows typical transient factors, in accordance with certain examples.

A procedure to account for the transients is now described with reference to FIG. 12. In FIG. 12, the curve 1240 represents the heat flow trace, the curves 1241 and 1243 represent the transients and the heat flow offset due to the change in scan rate and the curve 1232 represents the temperature ramp. The obtained isothermal baseline is subtracted from the heat flow trace 1240. The obtained scan baseline is then subtracted, and the remainder of the heat flow trace represents the transients. The transients can be grouped according to transition direction and then normalized by dividing by the scan rate. Principal components analysis as a function of time is then used typically retaining the first two factors as illustrated in FIG. 13. A curve 1346 represents one factor and a curve 1347 represents another factor. The factors are expressed as a function of temperature using a fifth order polynomial approximation. Each transient can be approximated to good accuracy by a linear combination of the two curves. The transients persist for an infinite length of time and are typically truncated after a reasonable time. An offset equal to the final value of each transient is subtracted from the transient to ensure that no step is observed when the transient is later added to the reconstructed baseline.

In the manner described above, mathematical functions representing three different baseline components can be used to reconstruct a baseline for given scan and temperature parameters.

When introducing elements of the examples disclosed herein, the articles "a," "an," and "the" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain features, aspects, examples and embodiments have been described above, additions, substitutions, modifications, and alterations of the disclosed illustrative features, aspects, examples and embodiments will be readily recognized by the person of ordinary skill in the art, given the benefit of this disclosure. To the extent that the meaning of any terms in the publications incorporated herein by reference conflict with those used in the instant disclosure, the meaning of the terms in the instant disclosure are intended to be controlling. For example, the term "sample" may refer to sample specimen alone or to a specimen encapsulated in a wide range of "pans", crucibles, foils, etc. In general, when running an encapsulated sample a pan of a similar type but empty will reside on the reference side of the DSC. "In the absence of a sample" or "no sample present" can refer to running the DSC with or without an empty pan in each sample position of the DSC, or even running the DSC with an inert reference material in the sample position or in both sample and reference positions to create a reference baseline relative to which a new sample will be measured.

The invention claimed is:

1. A differential scanning calorimeter comprising:
   a sample holder thermally coupled to a first furnace;
   a reference holder thermally coupled to a second furnace;
   a processor electrically coupled to the first furnace and the second furnace, the processor configured to receive data during a scan of a sample to provide a heat flow trace and further configured to subtract a calculated baseline from the heat flow trace, the calculated baseline comprising the sum of an isothermal baseline function, a scanning baseline function, and a transient baseline function to represent a plurality of instances of transients produced in a scan of a sample, wherein the processor determines the transient baseline function using principle components analysis, and wherein the processor calculates at least two principle component factors for the transient baseline function, which are expressed as functions of temperature.

2. The differential scanning calorimeter of claim 1, in which the processor is further configured to receive data during a scan in the absence of a sample to provide a background heat flow trace, to express as mathematical functions at least the isothermal and scanned components of the background heat flow trace, and to store the mathematical functions of the isothermal baseline function and the scanning baseline function.

3. The differential scanning calorimeter of claim 2, in which the processor is further configured to calculate a baseline using the stored mathematical functions.

4. The differential scanning calorimeter of claim 2, in which the stored mathematical functions for each of the isothermal and scanned components are fifth order polynomials.

5. The differential scanning calorimeter of claim 1, further comprising a first temperature sensor in the first furnace and a second temperature sensor in the second furnace, each of the first and second temperature sensors electrically coupled to the processor.

6. A differential scanning calorimeter comprising:
a furnace comprising a sample space, a reference space, a first heating element in thermal communication with the sample space and a second heating element in thermal communication with the reference space; and
a processor electrically coupled to the first and second heating elements and configured to detect a difference in power provided to the first and second heating elements at each of a plurality of different temperatures within a temperature range to provide a heat flow trace in the absence of a sample and within the temperature range, the processor further configured to provide a mathematical fit for isothermal, scanned, and transient components of the heat flow trace in which the transient mathematical fit is representative of a plurality of instances of transients produced in a scan of a sample, wherein the transient mathematical fit is determined using principle components analysis, and wherein the transient mathematical fit includes at least two principal component factors expressed as functions of temperature.

7. The differential scanning calorimeter of claim 6, further comprising a computer readable medium electrically coupled to the processor and configured to store the provided mathematical fit for each of an isothermal, a scanned and a transition portion of the heat flow trace.

8. The differential scanning calorimeter of claim 6, in which the processor is further configured to generate a baseline using the mathematical fit for each of the isothermal, the scanned and the transition components of the heat flow trace and to subtract the generated baseline from a sample heat flow trace obtained in the presence of a sample.

9. The differential scanning calorimeter of claim 6, in which the mathematical fit for each of the isothermal and scanned components is a fifth order polynomial.

10. A method of characterizing the baseline of a differential scanning calorimeter comprising:

using a differential scanning calorimeter to enerate measurements the differential scanning calorimeter comprising a sample holder thermally coupled to a first furnace, a reference holder thermally coupled to a second furnace, and a processor electrically coupled to the first furnace and the second furnace;
using the processor, generating data from measurements made with the calorimeter and generating a heat flow trace therefrom over each of a number of different temperature intervals with no sample present, the temperature being held constant a number of different temperatures for a time sufficient for thermal equilibrium to be achieved, and
using the processor, expressing as mathematical functions isothermal, scanned and transient components of the heat flow trace, wherein the transient function is expressed by subtracting from the heat flow trace the calculated isothermal and scanned functions, and analyzing the remainder using principal components analysis, wherein the transient function is calculated via the processor so that it includes at least two principal component factors expressed as functions of temperature, and wherein the transient function is representative of a plurality of instances of transients produced in a scan of a sample.

11. The method of claim 10, further comprising storing the mathematical functions on a computer readable medium.

12. The method of claim 10, wherein each of the isothermal and scanned components is expressed as a fifth order polynomial in temperature.

13. A method of determining a baseline in a differential scanning calorimeter, the method comprising:
using a differential scanning calorimeter to generate measurements, the differential scanning calorimeter comprising a sample holder thermally coupled to a first furnace, a reference holder thermally coupled to a second furnace, and a processor electrically coupled to the first furnace and the second furnace;
using the processor, generating data from measurements made with the calorimeter and generating a heat flow trace therefrom, and independently fitting a mathematical function to isothermal components and scanned components of the heat flow trace comprising a plurality of heat flow values obtained using no sample and holding the temperature constant at a number of different temperatures for a time sufficient for thermal equilibrium to be achieved for each of the heat flow values; and
using the processor, independently fitting a mathematical function to transient components of the heat flow trace, and generating a baseline using the fitted mathematical functions, in which the transient function is expressed by subtracting from the heat flow trace the calculated isothermal and scanned functions, and analyzing the reminder using principal components analysis, wherein the transient function is calculated via the processor so that it includes at least two principal component factors expressed as functions of temperature, and wherein the transient function is representative of a plurality of instances of transients produced in a scan of a sample.

14. The method of claim 13, in which the mathematical function fitted to each of the isothermal and scanned components is a fifth order polynomial.

15. The method of claim 13, in which the generated baseline is subtracted from a heat flow trace obtained in the presence of a sample.

16. The method of claim 13, in which the generated baseline is stored on a computer readable medium.

17. A method of performing calorimetric measurements in a differential scanning calorimeter, the method comprising:
  using a differential scanning calorimeter to generate measurements, the differential scanning calorimeter comprising a sample holder thermally coupled to a first furnace, a reference holder thermally coupled to a second furnace, and a processor electrically coupled to the first furnace and the second furnace;
  using the processor, generating data from measurements made with the calorimeter by scanning over a temperature range in the absence of a sample to generate a heat flow trace comprising a plurality of heat flow values obtained by holding the temperature constant at a number of different temperatures for a time sufficient for thermal equilibrium to be achieved for each of the heat flow values;
  using the processor, fitting an isothermal and a scanned portion of the heat flow trace to a mathematical function;
  using the processor, fitting a transient portion of the heat flow trace to a mathematical function;
  using the processor, storing the fitted mathematical functions; and
  using the stored fitted mathematical functions to generate a baseline signal for use in the calorimetric measurements, wherein the mathematical function for the transient portion is calculated using principal components analysis, and the mathematical function for the transient portion is calculated via the processor so that it includes at least two principal component factors expressed as functions of temperature, and wherein the mathematical function for the transient portion is representative of a plurality of instances of transients produced in a scan of a sample.

18. A differential scanning calorimeter comprising furnace means for heating a sample and a reference, and processing means coupled to the furnace means, the processing means having been calibrated by a method according to claim 10.

* * * * *